(12) United States Patent
Salvador Barea

(10) Patent No.: US 8,092,751 B2
(45) Date of Patent: Jan. 10, 2012

(54) ULTRAVIOLET AND/OR OZONE-GENERATING DISINFECTION DEVICE

(75) Inventor: Francisco Salvador Barea, Teruel (ES)

(73) Assignee: Kaparazoom, S.L.U., Valencia (ES)

( * ) Notice: Subject to any disclaimer, the term of this patent is extended or adjusted under 35 U.S.C. 154(b) by 0 days.

(21) Appl. No.: 12/995,846

(22) PCT Filed: Jun. 1, 2009

(86) PCT No.: PCT/ES2009/000305
§ 371 (c)(1),
(2), (4) Date: Dec. 2, 2010

(87) PCT Pub. No.: WO2009/147263
PCT Pub. Date: Dec. 10, 2009

(65) Prior Publication Data
US 2011/0085943 A1    Apr. 14, 2011

(30) Foreign Application Priority Data

Jun. 2, 2008 (ES) .................................. 200801816

(51) Int. Cl.
*B01J 19/08* (2006.01)
(52) U.S. Cl. .................................................. 422/186.3
(58) Field of Classification Search ................ 422/186.3
See application file for complete search history.

(56) References Cited

U.S. PATENT DOCUMENTS

| 5,225,172 A | 7/1993 | Meyler |
| 2006/0120915 A1* | 6/2006 | Lewandowski ................. 422/24 |

FOREIGN PATENT DOCUMENTS

| CN | 2380228 | 5/2000 |
| CN | 2584188 | 11/2003 |
| CN | 2671575 | 1/2005 |
| CN | 2673389 | 1/2005 |
| JP | 2000005284 | 1/2000 |
| JP | 2001037848 | 2/2001 |
| KR | 20080013735 | 2/2008 |
| WO | 0151098 | 7/2001 |

* cited by examiner

*Primary Examiner* — Kishor Mayekar
(74) *Attorney, Agent, or Firm* — Sturm & Fix LLP

(57) ABSTRACT

The ultraviolet and/or ozone-generation disinfection cutlery tray allows to improve the hygiene of the different cutlery items placed in it, by use of at least one ultraviolet light and/or ozone-generating source that irradiates the cutlery through the material itself making up the cutlery tray, made of a light-conductive plastic material, obtaining an homogeneous radiation, allowing objects that had been previously washed in a conventional way to maintain and conserve asepsis until the moment of use. Versions are contemplated for holding cutlery in vertical position, simultaneously allowing their drainage after washing and hygienization; and others in which the emission of ultraviolet light is located on the surface of the material making up the cutlery tray. The disinfection device is suitable for use for the domestic sector, catering industry, as well as the clinical sector.

7 Claims, 2 Drawing Sheets

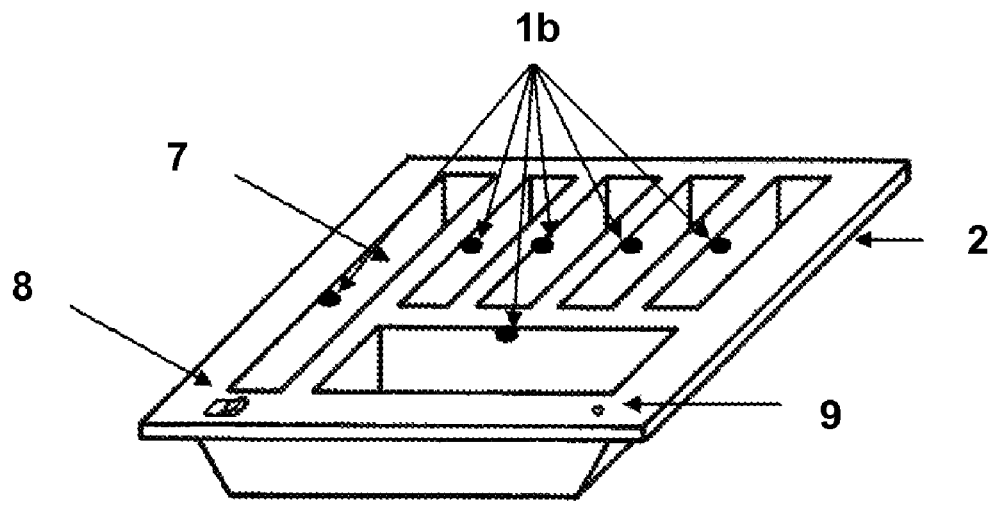
Figure 3
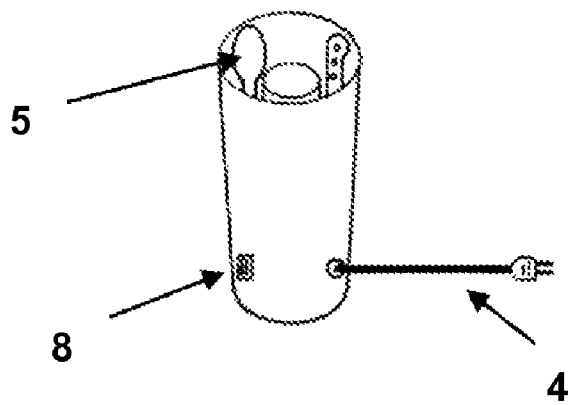 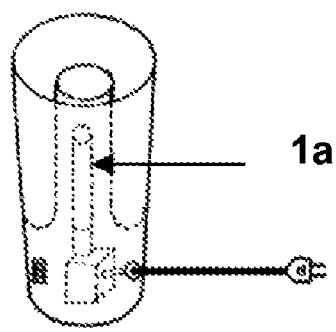
Figure 4  Figure 5

ULTRAVIOLET AND/OR OZONE-GENERATING DISINFECTION DEVICE

CROSS REFERENCE TO RELATED APPLICATIONS

This application is a national stage application of PCT/ES2009/000305 filed Jun. 1, 2009, claiming priority of Application No. ES200801816 filed Jun. 2, 2008, which are incorporated by reference herein in their entirety.

BACKGROUND OF THE INVENTION

1. Field of the Invention

The invention relates to the industrial sector of household goods, hotel supplies and to the hospital sector.

2. Description of the Related Art

Nowadays, cutlery is hygienized by using conventional cleaning procedures with detergents. After these procedures, the material is left in different supports or containers until used.

Generic devices for disinfection by use of ultraviolet radiation are known in the state of the art. In these devices, for radiation to diffuse uniformly, different external elements are usually applied, such as diffusors and reflective screens, or said source of ultraviolet emission is homogeneized and reflected by using another element of the container assembly that is also used as lid.

There are no known teachings in the state of the art of the incorporation of at least one ultraviolet light and/or ozone-generating source irradiating through a light-conductive material in cutlery-holding trays with the aim of maintaining asepsis of household utensils.

It would therefore be desirable to obtain a hygienic guarantee for houseware from the time when it is washed up until it is used, given that storage in today's cutlery trays intended to this end does not guarantee that gear placed in them is not contaminated by pathogen agents during said time period, this being of special relevance in clinical environments.

The integration of ultraviolet radiation and/or ozone-generation in the cutlery trays for houseware of the present invention allows to obtain a new final product satisfying the conditions required to guarantee the correct asepsis of cutlery.

For the above, the present invention offers an asepsis guarantee by the application of irradiation of at least one ultraviolet and/or ozone-generating light to said gear, using the light-conductive plastic material itself making up the cutlery tray for diffusing and homogenizing the ultraviolet radiation, the moulding thereof having cavities for specifically housing the cutlery.

SUMMARY OF THE INVENTION

The new cutlery tray provided with ultraviolet disinfection and/or ozone-generation comprises at least one source of ultraviolet radiation and/or ozone-generating source (1a) irradiating from the inside of the conventional cutlery-holding trays (2) (FIGS. 1 and 2). Another version of the ultraviolet disinfection and/or ozone-generating device irradiates from the surfaces of the light-conductive material itself of the device (1b) (FIG. 3). Another version of the ultraviolet radiation and/or ozone-generating device in which cutlery is placed vertically is contemplated, allowing its drainage after their conventional washing and irradiation with the source of ultraviolet light (1a) from the inside of said device (FIGS. 4 and 5).

The new ultraviolet and/or ozone-generating disinfection cutlery tray presents the novelty of using at least one ultraviolet light and/or ozone-generating source that irradiates from the inside of the cutlery trays, hygienizing the cutlery stored or contained in them. The new cutlery tray is made up of a plastic light-conductive material that is permeable to this radiation. As in the cutlery tray or dispenser (FIGS. 1 and 3) and in the cutlery-draining baskets (FIGS. 4 and 5). It offers the user greater sterilization safety because it takes advantage of the germicide action of the ultraviolet radiation and/or ozone-generation falling on the cutlery.

These cutlery trays (2) for holding or storing cutlery are preferably of plastic nature with light-conductive properties, allowing the light source (1a) to be conducted and irradiate uniformly the cavities for holding the gear. The nature of the light-conductive plastic can be obtained by combining two vitreous polymers having different refractive indices.

The light radiation source is fed by batteries (6) (FIG. 2) or directly from the electrical power grid (4) (FIG. 4). The activation periods of said radiation can be automated if necessary, using a conventional electronic circuitry.

In addition, with an aim to protecting the user from this potentially damaging light emission, different safety systems or devices (9) are used that block this radiation when the door of the chest of drawers (3) in which the light radiation source is installed is in an open state.

BRIEF DESCRIPTION OF THE SEVERAL VIEWS OF THE DRAWINGS

As a complement of the description being made and for a better understanding of the characteristics of the invention, attached to the present descriptive material and as an integral part of it is a set of drawings where, for purposes of illustration and in a non-limiting manner, the following is shown:

FIG. 3 shows the cutlery tray (2), in which the source of light radiation external to the tray (1b) can be seen, in which (7) are the cavities where the gear is housed, (8) represents a switch and (9), a safety element.

FIG. 4 shows a cutlery-draining support (5), fed to the electrical power grid (4) with its switch (8).

FIG. 5, the source of light radiation (1a) in the inside can be seen.

DETAILED DESCRIPTION OF THE INVENTION

Figure 1:
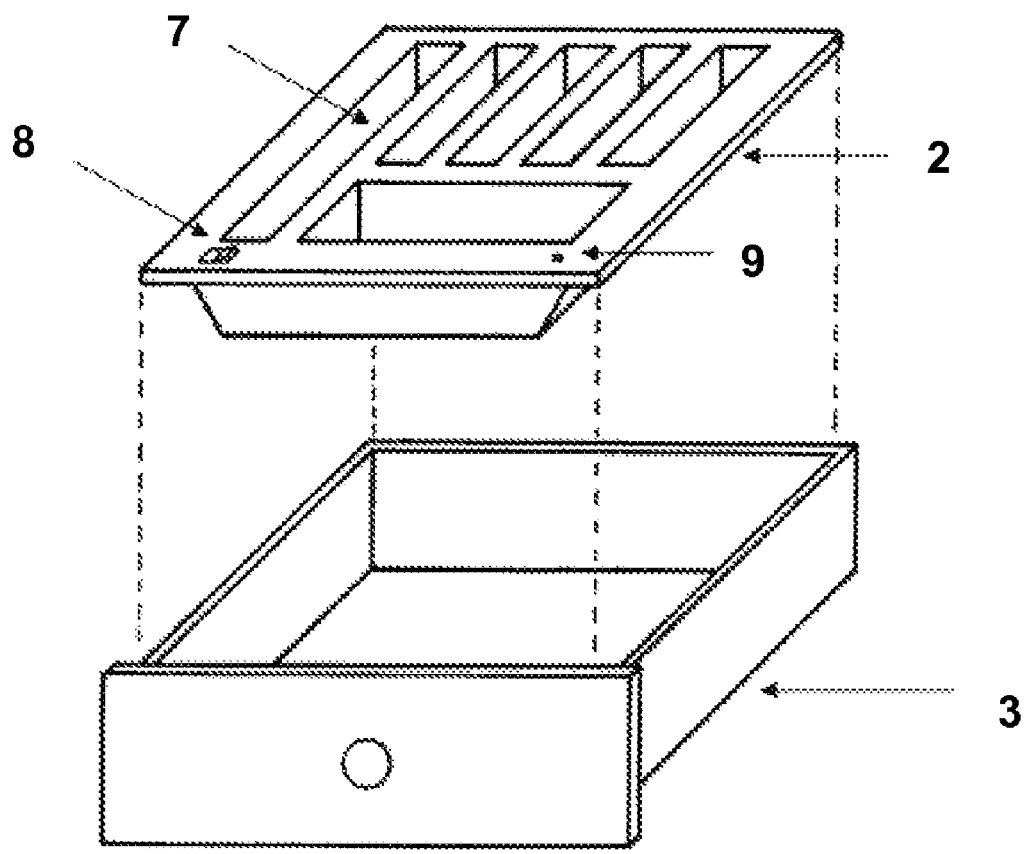
FIG. 1 shows the cutlery tray (2) before being placed in a conventional drawer (3), in which are the cavities (7) where the gear is housed, (8) represents a switch and (9), a safety element.
Figure 2:
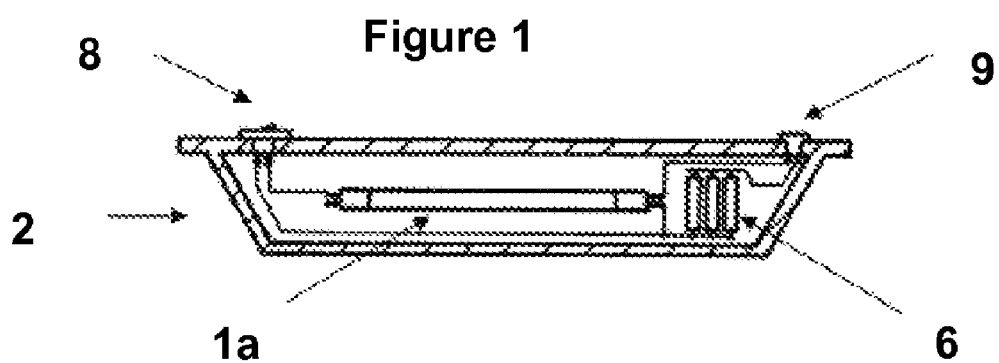
FIG. 2 shows a section of the cutlery-holding tray (2), in which the source of light radiation (1a) and the power source (6) can be seen in the inside; (8) represents a switch and (9), a safety element.

The ultraviolet and/or ozone-generating disinfection cutlery-holding tray for houseware described in the following preferred embodiment (FIGS. 1 and 2) comprises at least one ultraviolet light and/or ozone-generating source (1a) in the inside of a body of plastic light-conductive tray (2), i.e. permeable to said radiation, provided with a battery power source (6) housed in the plastic tray (2).

The previously-washed gear is placed in the cavities (7) in the tray (2). By activating the source of light radiation, radiation is emitted from the ultraviolet and/or ozone-generating source (1a), to the cavities or housings (7) of the tray, distributing the light radiation in an homogeneous manner over the surfaces of the support of a light-conductive plastic material, which could be a vitreous polymer such as polymethacrylate, the surface thereof being coated with another polymer having a different refractive index, obtaining this coating, for example, by submerging the cutlery tray in this second polymer and a later oven treatment to volatilize solvents used in the process.

The activation of the ultraviolet and/or ozone-generating disinfection cutlery tray for houseware is performed by use of a conventional switch (8) and a LDR (light diode resistance) sensor (9), which turns on a light source only in the case that the drawer is closed, thus preventing radiation exposure to the user.

The materials, shape, size and arrangement of the elements may be modified as long as this does not imply altering the essential characteristics of the claimed invention.

The invention claimed is:

1. A disinfection device, comprising:
   a tray including a cavity for holding utensils, the tray being formed of a light-conductive material formed by the combination of two vitreous polymers having different refractive indices;
   an irradiation device, selected from the group consisting of an ultraviolet light and an ozone-generating light, the irradiation device being disposed to distribute light radiation through the light-conductive material in an homogenous manner into the cavity of the tray.

2. The device of claim 1, wherein the tray has a body, including an exterior surface formed of a first vitreous-polymer having a first refractive index, wherein the surface is coated with a second vitreous polymer having a second refractive index different from the first refractive index.

3. The device of claim 2, wherein the first vitreous polymer is polymethacrylate.

4. The device of claim 1, wherein the irradiation device is disposed in spaced relationship from the cavity of the tray.

5. The device of claim 4, wherein the utensils in the cavity are horizontally disposed.

6. The device of claim 4, wherein the utensils in the cavity are vertically disposed to facilitate draining.

7. The device of claim 1, wherein the irradiation device is disposed within the cavity of the tray.

* * * * *